United States Patent
Liu et al.

(10) Patent No.: US 11,828,169 B2
(45) Date of Patent: Nov. 28, 2023

(54) METHOD OF DETERMINING IN-SITU PORE PRESSURE IN CHEMICALLY ACTIVE FORMATIONS

(71) Applicant: SAUDI ARABIAN OIL COMPANY, Dhahran (SA)

(72) Inventors: Chao Liu, Brookshire, TX (US); Dung Phan, Brookshire, TX (US); Katherine Hull, Houston, TX (US); Younane Abousleiman, Norman, OK (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 114 days.

(21) Appl. No.: 17/096,285

(22) Filed: Nov. 12, 2020

(65) Prior Publication Data

US 2022/0145751 A1    May 12, 2022

(51) Int. Cl.
    *E21B 47/06*       (2012.01)
    *G06F 30/10*       (2020.01)
                (Continued)

(52) U.S. Cl.
    CPC .............. *E21B 47/06* (2013.01); *G01N 33/24* (2013.01); *G01V 5/12* (2013.01); *G01V 99/005* (2013.01); *G06F 30/10* (2020.01)

(58) Field of Classification Search
    CPC ......... E21B 47/06; E21B 49/00; G01N 33/24; G01V 5/12; G01V 99/005; G06F 30/10
See application file for complete search history.

(56) References Cited

U.S. PATENT DOCUMENTS

| 4,743,854 A | 5/1988 | Vinegar et al. |
| 4,903,527 A | 2/1990 | Herron |
| (Continued) | | |

FOREIGN PATENT DOCUMENTS

| CN | 104563927 A | * | 4/2015 | ............ E21B 49/00 |
| GB | 2272525 A | | 5/1994 | |
| WO | 2020072367 A1 | | 4/2020 | |

OTHER PUBLICATIONS

Nguyen, Vinh; "Incorporating Electrokinetic Effects in the porochemoelastic inclined wellbore formulation and solution", Annals of the Brazilian Academy of Sciences, Sep. 10, 2008 (Year: 2008).*

(Continued)

*Primary Examiner* — Catherine T. Rastovski
*Assistant Examiner* — Yossef Korang-Beheshti
(74) *Attorney, Agent, or Firm* — Osha Bergman Watanabe & Burton LLP (57) ABSTRACT

Methods for determining an in-situ pore pressure in a formation rock may include acquiring well log data, calculating a cation-exchange capacity, calculating a mole fraction of fixed charges using the cation-exchange capacity, determining a formation temperature, calculating the in-situ pore pressure, outputting the in-situ pore pressure of the formation rock, and using the in-situ pore pressure in a wellbore stability model to monitor and maintain stability of the formation rock. Corresponding electronic devices may include a computer processor coupled to at least one logging tool, wherein the logging tool is configured to acquire well log data in a formation rock. Non-transitory computer storage mediums may include program instructions, that when executed, may be configured to perform the methods for determining an in-situ pore pressure in a formation rock.

11 Claims, 8 Drawing Sheets

(51) Int. Cl.
  *G01N 33/24* (2006.01)
  *G01V 5/12* (2006.01)
  *G01V 99/00* (2009.01)

(56) References Cited

U.S. PATENT DOCUMENTS

| | | | |
|---|---|---|---|
| 5,282,384 | A | 2/1994 | Holbrook |
| 5,285,692 | A | 2/1994 | Steiger et al. |
| 5,965,810 | A | 10/1999 | Holbrook |
| 6,434,487 | B1 | 8/2002 | Thompson |
| 2010/0018702 | A1 | 1/2010 | Cook et al. |
| 2012/0192640 | A1 | 8/2012 | Minh et al. |
| 2015/0197685 | A1* | 7/2015 | Southwick ............. C09K 8/584 507/224 |
| 2015/0267527 | A1* | 9/2015 | Nguyen ................... G01V 3/20 702/12 |
| 2016/0376887 | A1 | 12/2016 | Hayatdavoudi et al. |
| 2017/0235016 | A1* | 8/2017 | Prioul ................... E21B 49/005 73/152.01 |
| 2022/0043176 | A1* | 2/2022 | Sayers ..................... G01V 1/50 |

OTHER PUBLICATIONS

Drilling Formulas, www.drillingformulas.com/understand-about-formation-pressure/, Oct. 30, 2009 (Year: 2009).*
Encyclopaedia Britannica, "Mineralogy", Mar. 10, 2018 (Year: 2018).*
Y. Abousleiman et al. "Geomechanics Field and Laboratory Characterization of Woodford Shale: The Next Gas Play" Society of Petroleum Engineers; Anaheim, California; Nov. 11-14, 2007 (14 pages).
Y. Abousleiman et al. "GeoMechanics Field Characterization of the Two Prolific U.S. Mid-West Gas Plays With Advanced Wire-Line Logging Tools" Society of Petroleum Engineers; New Orleans, Louisiana; Oct. 4-7, 2009 (19 pages).
G. Bowers et al. "Pore Pressure Estimation From Velocity Data: Accounting for Overpressure Mechanisms Besides Undercompaction" Society of Petroleum Engineers; Jun. 1995 (7 pages).
G. E. Christidis "Industrial Clays" EMU Notes in Mineralogy; vol. 9, Chapter 9 (76 pages).
B. Eaton "The Equation for Geopressure Prediction from Well Logs" Society of Petroleum Engineers of AIME; Dallas, TX, USA; Sep. 28-Oct. 1, 1975 (11 pages).
C. Liu et al. "Theory and Analytical Solutions to Coupled Processes of Transport and Deformation in Dual-Porosity Dual-Permeability Poro-Chemo-Electro-Elastic Media" Journal of Applied Mechanics. vol. 85; Nov. 2018 (13 pages).
V. Nguyen et al. "Incorporating electrokinetic effects in the porochemoelastic inclined wellbore formulation and solution" Anais da Academia Brasileira de Ciências. 82(1) (28 pages).
J. T. Krushin "A True Shale Compaction Model with Pore Pressure Prediction" Offshore Technology Conference; Houston, Texas, USA; May 6-9, 2013 (12 pages).
S. M. Haugland et al. "Cation Exchange Capacity Effects On Resistivity-Based Pore Pressure Predictions" SPWLA 49th Annual Logging Symposium; Edinburgh, Scotland; May 25-28, 2008 (11 pages).
A. Ghassemi et al. "Effects of Ion Transfer on Stress and Pore Pressure Distributions Around a Borehole in Shale" The 38th U.S. Symposium on Rock Mechanics, DC Rocks 2001: ARMA-01-0085 Jul. 7, 2001 (8 pages).
International Search Report and Written Opinion issued in corresponding PCT International Application No. PCT/US2021/059131 dated Mar. 28, 2022 (130 pages).

* cited by examiner

```
┌─────────────────────────────────┐
│ Acquire well log data from at   │
│ least one nuclear logging tool  │──410
└─────────────────────────────────┘
              ⇩
┌─────────────────────────────────┐
│ Calculate a cation-exchange     │
│ capacity using a volume         │
│ fraction and a cation-          │──420
│ exchange capacity for each      │
│ mineral in the formation rock   │
│ at a plurality of depths        │
└─────────────────────────────────┘
              ⇩
┌─────────────────────────────────┐
│ Calculate a mole fraction of    │
│ fixed charges using the cation- │
│ exchange capacity, a porosity   │
│ of the formation rock, a grain  │──430
│ density of the formation rock,  │
│ and a water molar volume at a   │
│ plurality of depths             │
└─────────────────────────────────┘
              ⇩
┌─────────────────────────────────┐
│ Determine a formation           │
│ temperature at a plurality of   │──440
│ depths                          │
└─────────────────────────────────┘
              ⇩
┌─────────────────────────────────┐
│ Calculate the in-situ pore      │
│ pressure using the mole         │
│ fraction of fixed charges, the  │
│ formation temperature, a        │
│ surface temperature, a          │──450
│ hydrostatic pressure, an        │
│ overburden stress, and an       │
│ in-situ water activity at a     │
│ plurality of depths             │
└─────────────────────────────────┘
              ⇩
┌─────────────────────────────────┐
│ Output in-situ pore pressure    │──460
└─────────────────────────────────┘
              ⇩
┌─────────────────────────────────┐
│ Use of in-situ pore pressure in │
│ a wellbore stability model to   │──470
│ monitor and maintain stability  │
│ of the formation rock           │
└─────────────────────────────────┘
```

METHOD OF DETERMINING IN-SITU PORE PRESSURE IN CHEMICALLY ACTIVE FORMATIONS

BACKGROUND

In the oil and gas industry, formation pore pressure is an important factor to consider for the design of drilling, hydraulic fracturing, and production operations of an oil and gas well. In particular, the determination of pore pressure may avoid the risk of a blowout resulting from an excessive formation pore fluid pressure relative to the borehole fluid hydrostatic pressure. Pore pressure is exerted on fluids within the pores of a reservoir rock or other porous formations.

There exist various methods to estimate pore pressure, such as Eaton's method, the equivalent depth method, and the ratio method.

Eaton's method relies on the following Equation (1):

$$p = \sigma_v - (\sigma_v - p_{hyd})\left(\frac{R_{measured}}{R_{normal}}\right)^{1.2} \quad (1)$$

where p is the pore pressure, $\sigma_v$ is the overburden stress, $p_{hyd}$ is the hydrostatic pressure, $R_{measured}$ is the measured resistivity, and $R_{normal}$ is the normal resistivity.

The equivalent depth method may be expressed by Equation (2):

$$p_D = p_{D_0} + (\sigma_{vD} - \sigma_{vD_0}) \quad (2)$$

where p and $\sigma_v$ are the pore pressure and overburden stress, respectively, D is the depth of interest, and $D_0$ is some depth along the normal compaction trend.

The ratio method may be expressed according to Equation (3):

$$p = \frac{p_{hyd} R_{normal}}{R_{measured}} \quad (3)$$

Claystone and shales are sediments that are often responsible for overpressure generation. In addition, clay content in a rock formation might serve as a semipermeable membrane as the clay impedes the transportation of solutes of a solution. Thus, when clay and shale formations are exposed to environmental solutions, an osmotic pressure may result. In chemically active formations, chemo-osmotic pressure could contribute to abnormal pressure adding to the hydraulic pressure resulting in a higher in-situ pore pressure.

SUMMARY

In one aspect, embodiments disclosed herein are directed to methods for determining an in-situ pore pressure in a formation rock. The methods may include acquiring well log data from at least one logging tool. They may also include calculating a cation-exchange capacity using a volume fraction and a cation-exchange capacity for each mineral in the formation rock. The methods may also include calculating a mole fraction of fixed charges using the cation-exchange capacity, a porosity of the formation rock, a grain density of the formation rock, and a water molar volume. The methods may further include determining a formation temperature. They may include calculating the in-situ pore pressure using the mole fraction of fixed charges, the formation temperature, a surface temperature, a hydrostatic pressure, an overburden stress, and an in-situ water activity. The methods may further include outputting the in-situ pore pressure of the formation rock and using the in-situ pore pressure in a wellbore stability model to monitor and maintain stability of the formation rock.

In another aspect, embodiments disclosed herein are directed to electronic devices including a computer processor coupled to at least one logging tool, wherein the logging tool is configured to acquire well log data in a formation rock. The electronic devices may include functionality for acquiring well log data from at least one logging tool. They may also include functionality for calculating a cation-exchange capacity using a volume fraction and a cation-exchange capacity for each mineral in the formation rock. The electronic devices may further include functionality for calculating a mole fraction of fixed charges using the cation-exchange capacity, a porosity of the formation rock, a grain density of the formation rock, and a water molar volume. The electronic devices may include functionality for determining a formation temperature. They may include functionality for calculating the in-situ pore pressure using the mole fraction of fixed charges, the formation temperature, a surface temperature, a hydrostatic pressure, an overburden stress, and an in-situ water activity. The electronic devices may include functionality for outputting the in-situ pore pressure of the formation rock and using the in-situ pore pressure in a wellbore stability model to monitor and maintain stability of the formation rock.

In another aspect, embodiments disclosed herein are directed to corresponding non-transitory computer storage mediums including program instructions, that when executed, are configured to perform the methods for determining an in-situ pore pressure in a formation rock.

Other aspects and advantages of the invention will be apparent from the following description and the appended claims.

BRIEF DESCRIPTION OF DRAWINGS

The following is a description of the figures in the accompanying drawings. In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn are not necessarily intended to convey any information regarding the actual shape of the particular elements and have been solely selected for ease of recognition in the drawing.

DETAILED DESCRIPTION

In the following detailed description, certain specific details are set forth in order to provide a thorough understanding of various disclosed implementations and embodiments. However, one skilled in the relevant art will recognize that implementations and embodiments may be practiced without one or more of these specific details, or with other methods, components, materials, and so forth. In other instances, well known features or processes associated with hydrocarbon production systems have not been shown or described in detail to avoid unnecessarily obscuring descriptions of the implementations and embodiments. For the sake of continuity, and in the interest of conciseness, same or similar reference characters may be used for same or similar objects in multiple figures.

In this disclosure, terms "well," "oil well," "gas well," "oil and gas well," and like terms may be used interchangeably without narrowing the type of well unless specifically stated.

In this disclosure, an environmental solution is an aqueous solution present in rock formations, such as clayey formations. The environmental solution occupies the pore spaces in the rock formations. The aqueous solution may include water, anions, cations, and/or hydrated solutes.

Determining the formation pore pressure is an important aspect of exploration drilling. In particular, in clayey formations, when exposed to environmental solutions, the clay may impede the transportation of solutes of the solutions and generate an osmotic pressure that may be expressed by Equation (4):

$$p_{osomotic} = \chi \frac{RT}{V_0^f} \ln \frac{a_{env}}{a_0} \quad (4)$$

where $\chi$, (dimensionless), is the membrane efficiency;

$$R, \left(\frac{m^3 \cdot Pa}{mol \cdot °K}\right),$$

is the gas constant; T, (° K), is the absolute temperature;

$$V_0^f, \left(\frac{m^3}{mol}\right),$$

is the partial molar volume of water; $\alpha_{env}$ and $\alpha_0$, (dimensionless), are the water activities of the environmental solution and the chemically active rock formation, respectively.

While Equation (4) is an estimation of the osmotic pressure generated by clay contents in rock formations, it does not take into account the different degrees of impedance on the transportation of anions and cations resulting from the negatively charged clay surfaces. Embodiments herein provide a method determining pore pressure accounting for this difference.

A method for determining in-situ pore pressure in a formation rock while drilling is presented. The method provides for the acquisition of well log data and the calculation of parameters using the well log data to arrive at the in-situ pore pressure. In particular, the method includes the determination of a number of parameters such as the cation-exchange capacity, the mole fraction of fixed charges, the porosity of the formation rock, the grain density of the formation rock, the formation temperature, the hydrostatic pressure, and the water activity.

Figure 1:
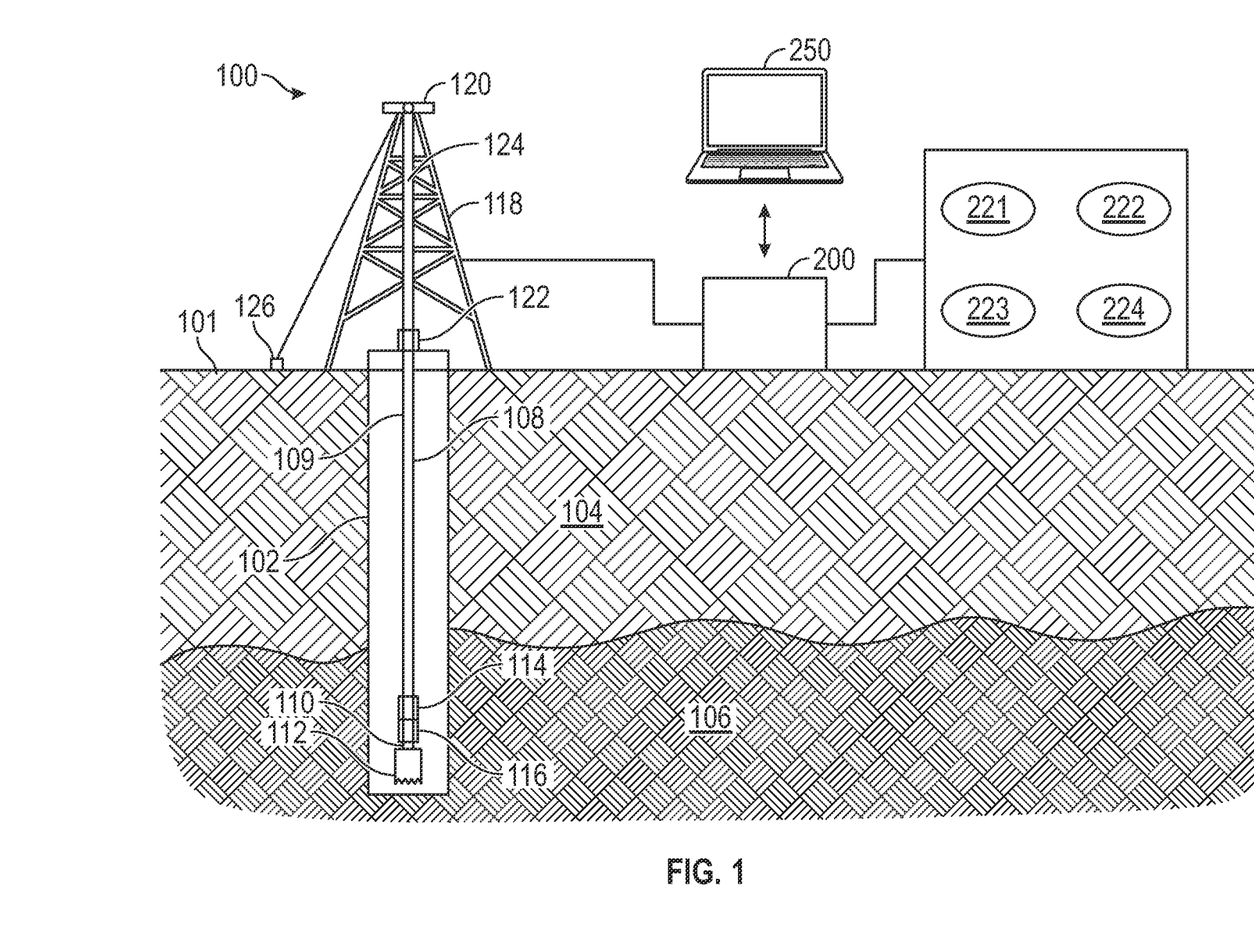
FIG. 1 is a schematic diagram of an exemplary well site in accordance with one or more embodiments.

FIG. 1 is a diagram that illustrates an exemplary well site 100. In general, well sites may be configured in a myriad of ways. Therefore, well site 100 is not intended to be limiting with respect to the particular configuration of the drilling equipment. Well site 100 is depicted as being on land. In other examples, well site 100 may be offshore, and drilling may be carried out with or without use of a marine riser. A drilling operation at well site 100 may include drilling a wellbore 102 into a subsurface including various formations, such as formations 104 and 106 residing underground, beneath the surface 101 of the Earth. The formations 104 and 106 may each include different layers of rock having varying characteristics, such as degree of density, permeability, porosity, and fluid saturations.

For the purpose of drilling a new section of wellbore 102, a drill string 108 is suspended within wellbore 102. Drill string 108 may include one or more drill pipes 109 connected to form conduit and a bottom hole assembly (BHA) 110 disposed at the distal end of the conduit. The BHA 110 may include a drill bit 112 to cut into the subsurface rock. The BHA 110 and drill string 108 may include other drilling tools known in the art but not specifically shown.

Drill string 108 may be suspended in wellbore 102 by a derrick 118. A crown block 120 may be mounted at the top of derrick 118, and a traveling block 122 may hang down from crown block 120 by means of a cable or drilling line 124. One end of cable 124 may be connected to a drawworks 126, which is a reeling device that can be used to adjust the length of cable 124 so that traveling block 122 moves up or down derrick 118.

Drilling operations for the well site 100 may include a well logging operation to generate a well log for the well 102. Well logging of the well site 100 may include logging tools 114 and 116 to generate the well log including, for example, a gamma ray log, an Elemental Capture Spectroscopy (ECS) log, an X-ray diffraction (XRD) log, a photoelectric factor log, a porosity log, a neutron porosity log, mineralogy log, and/or a density log. These logging tools may include nuclear logging tools that may be placed in the wellbore 102 and operated to detect characteristics of the wellbore 102. Logging tools 114 and 116 may include sensors and hardware to measure downhole drilling or wellbore (formation) parameters, and these measurements may be transmitted to the surface using any suitable telemetry system known in the art. The illustrated number and locations of logging tools 114 and 116 are not intended to be limiting, and logging tools 114 and 116 could be lowered and disposed in the wellbore 102 wherever formation parameters need to be measured. Moreover, there may be many more logging tools than shown in FIG. 1 to measure various other parameters of the layers of the rock formations 104 and 106. Each logging tool 114 or 116 may be configured to measure a desired physical property.

In one implementation, a system 200 may be disposed at or communicate with well site 100. System 200 may regulate various operations of the well site 100, such as well drilling operations, well completion operations, well production operations or well or formation monitoring operations. In some embodiments, the system 200 is configured to relay information, such as the log data from logging tools 114 and 116 to a control terminal 250. The information may be numerically or graphically displayed, or both. An external viewer may include a computer monitor, a television, a printer, or any other form of temporal or permanent version of record keeping and displaying that can be visually appreciated.

In some additional embodiments, the system 200 may utilize some or all of the information from the logging tools 114 and 116, in addition to a set of pre-determined instructions and algorithms retained in the memory of a computer system, to provide calculated data 221, 222, 223, and 224. These calculated data include, in some embodiments, the cation-exchange capacity (CEC), the mole fraction of fixed charges, the formation temperature, and the in-situ pore pressure for different minerals in the different layers of rock formations 104 and 106.

Figure 2:
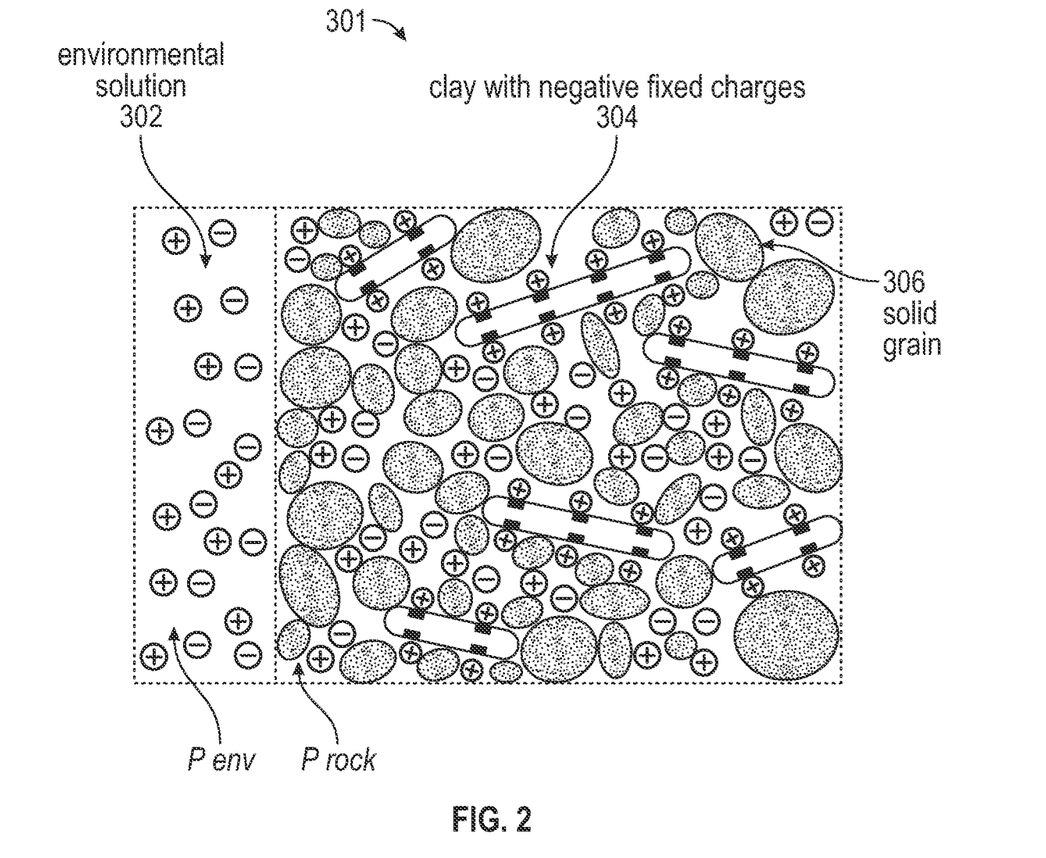
FIG. 2 is a schematic diagram of a chemically active rock sample exposed to an environmental solution in accordance with one or more embodiments.

FIG. 2 illustrates a chemically active rock sample 301 exposed to an environmental solution 302 in accordance with one or more embodiments. The rock sample 301 contains clay 304 having negative fixed charges. The rock sample 301 also contains solid grains 306. $p_{env}$ represents the hydraulic pressure of the environmental solution and $p_{rock}$ represents the rock pore pressure.

The individual electrochemical potentials of the anionic components, cationic components and water present in a chemically active rock sample are defined by Equation (5):

$$\mu^l = pV^l + RT\ln(m^l) + z^l F\psi \quad (5)$$

where fluid component l may be an anionic component, a cationic component, or water (a, c, w respectively); $\mu^l$ is the electrochemical potential of fluid component l; p is the hydraulic pressure; $V^l$ is the partial molar volume of fluid component l; $m^l$ is the concentration of fluid component l; $z^l$ is the valence of ionic component; F is the Faraday constant; and $\psi$ is the electrical potential.

When the system is in equilibrium, the electrochemical potentials of the same fluid component in the sample and outer solution must equal as expressed in Equation (6):

$$\mu_{env}^l = \mu_{rock}^l \quad (6)$$

Furthermore, in view of the electrical neutrality conditions, the valence of ionic components and their mole fractions are governed by Equation (7):

$$z^a m^a + z^c m^c + z^{fc} m^{fc} = 0 \quad (7)$$

where $m^a$, $m^c$, and $m^{fc}$ are the mole fractions of anion, cation, and the fixed charges on clay surfaces, respectively.

Equations (8) and (9) may result from solving equations (5-7), $$m^a = \tfrac{1}{2}[-m^{fc} + \sqrt{(m^{fc})^2 + (1-\alpha_{env})^2}] \quad (8)$$

$$m^c = \tfrac{1}{2}[m^{fc} + \sqrt{(m^{fc})^2 + (1-\alpha_{env})^2}] \quad (9)$$

The osmotic pressure generated in the rock may be calculated according to Equations (10) and (11): i.e., $$p_{osmotic} = \frac{RT}{V_0^f}[m^a + m^c - (1 - a_{env})] \quad (10)$$

$$p_{osmotic} = \frac{RT}{V_0^f}\left[\sqrt{(m^{fc})^2 + (1-a_{env})^2} - (1-a_{env})\right] \quad (11)$$

The mole fraction of fixed charges, i.e., $m^{fc}$, on clay surfaces is highly controlled by formation Cation Exchange Capacity (CEC). Nguyen V., and Abousleiman Y., Incorporating electrokinetic effects in the porochemoelastic inclined wellbore formulation and solution. Anais da Academia Brasileira de Ciências., 2010, 2(1): 195-222, provided the following formula in Equation (12) to calculate $m^{fc}$:

$$m^{fc} = \frac{10CEC(1-\phi)\rho_s V_0^f}{\phi} \quad (12)$$

where CEC is the Cation Exchange Capacity (milli-equivalent of cations per 100 grams of dry clay, meq/100 g), $\phi$ is the porosity, $\rho_s$ is the grain density (g/cc), $V_0^f$ is the water molar volume (m³/mol).

CEC is the total capacity of a rock formation to hold exchangeable cations. Clay and organic matter have relatively high CEC, where different clay minerals may have different values of CEC. For instance, Christidis G., Industrial clays. EMU Notes in Mineralogy, Vol. 9, Chapter 9, 341-414 (2011) provided values of CEC for various clay minerals as shown by Table 1. CEC for organic matter is in the range of 130-500 meq/100 g.

TABLE 1

| Minerals | Kaolinite | Illite and Chlorite | Smectite | Vermiculite |
|---|---|---|---|---|
| CEC (meq/100 g) | 1-15 | 10-40 | 70-150 | 130-210 |

In-situ pore pressure may be expressed by Equation (13):

$$p_{insitu} = p_{hyd} + p_{abnormal} \quad (13)$$

In chemically active formations, chemo-osmotic pressure could contribute to the abnormal pressure, as shown by Equation (11). However, Equation (11) neglects the effects of confining pressure. And, subsurface formations are under high compressional stresses. Therefore, Equation (11) may be modified to take into account the effects of compressional stresses, which increase with depth. Accordingly, the following formula shown in Equation (14) provides a more accurate calculation of formation in-situ pore pressure at a depth of interest:

$$p_{insitu} = p_{hyd} + (\sigma_v - p_{hyd})\frac{T}{T_{surface}}\left[\sqrt{(m^{fc})^2 + (1-a_{insitu})^2} - (1-a_{insitu})\right]^n \quad (14)$$

where $\alpha_{insitu}$ is the in-situ water activity, T is the temperature at the depth of interest which can be calculated according to Equation (15)

$$T = T_{surface} + Depth \times Geothermal\ Gradient \quad (15)$$

For example, if the geothermal gradient is chosen as 298.15 K/km, in Equation (15), parameter n can be determined from field data. For example, the field data presented in Table 1 by Eaton B., the equation for geopressure prediction from well logs, Paper presented at Fall Meeting of the Society of Petroleum Engineers of AIME, 28 Sep.-1 Oct. 1975, Dallas, TX, USA, may be used to calculate n. When CEC=10 meq/100 g, $\phi$=0.19, $\rho_s$=2.7 g/cc, and $V_0^f$=18×10⁻⁶ m³/mol, the concentration of the fixed charge can be calculated to be $m^{fc}=0.062$ from equation (12). Next if the water activity is equal to 0.7, we can calculate the term, $\sqrt{(m^{fc})^2+(1-\alpha_{insitu})^2}-(1-\alpha_{insitu})$, in equation (14) to be 0.0063. Suppose the true vertical depth is 1000 m, we have $p_{hyd}=\rho_{water}gD=9.8$ MPa, and $\sigma_v=[\phi\rho_f+(1-\phi)\rho_s]gD=23.3$ MPa. Assume the surface temperature is 298 K, i.e., $T_{surface}=298$ K. Then using equation (15), we have T=596.15 K. Further using the field data from Table 1 in Eaton (1975), i.e., $p_{insitu}=12.7$ MPa at 1000 m and substituting the parameters into equation (14) give the following equation: $12.7=9.8+27\times0.062^n$, based on which n can be calculated to be around 0.8.

The information or log data that is obtained from logging tools 114 and 116 in well using system 200 includes porosity of the formation rock, grain density of the formation rock, water molar volume, formation temperature. This log data, together with field data and known constants and parameters may be used as in Equations (5)-(15) in order to determine in-situ pore pressure in the formation rock.

Figure 3:
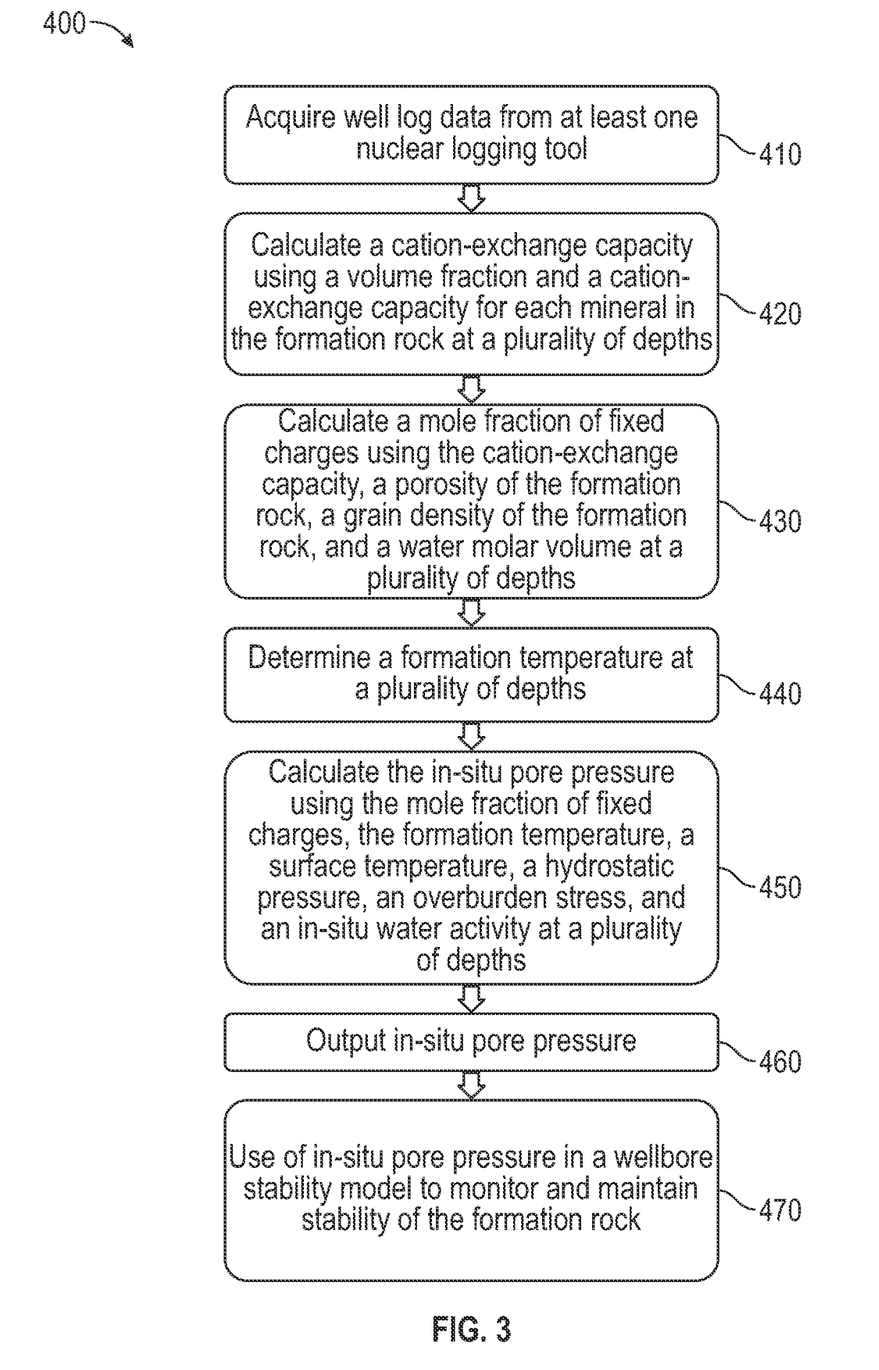
FIG. 3 is a flowchart describing a method in accordance with one or more embodiments.

FIG. 3 is a flowchart that illustrates an embodiment method 400 of determining an in-situ pore pressure in a formation rock. Referring to FIG. 3, in some embodiments, the method 400 may include acquiring well log data from at least one logging tool (block 410). For example, a gamma ray log obtained from a nuclear logging tool may be used to determine clay content in the rock formation. In addition, Elemental Capture Spectroscopy (ECS) log or X-ray diffraction (XRD) mineralogy analysis may be used to determine mineral types and their volume fractions in the rock formation. Alternatively, the photoelectric factor, density, and neutron porosity logs may be used to determine minerals and their volume fractions in the rock formation. In some embodiments, the method 400 includes calculating the CEC using a volume fraction and a CEC for each mineral in the formation rock at a plurality of depths (block 420). In particular, the CEC may be calculated based on Table 1 using Equation (16)

$$CEC=\Sigma v_r CEC_r \qquad (16)$$

where $v_r$ and $CEC_r$ are the volume fraction and CEC of mineral r, respectively. The CEC values presented in Table 1 are based on published papers. From the ranges of CEC for each minerals in the formation in Table 1, the average values of the CEC for each minerals can be selected. For example, the average values of the CEC for the following minerals can be chosen CEC=8 meq/100 g for Kaolinite, 25 meq/100 g for Illite and Chlorite, 110 meq/100 g for Smectite, and 170 meq/100 g for Vermiculite.

In some embodiments, the method 400 may include calculating the mole fraction of fixed charges at a plurality of depths using Equation (12) using the CEC, the porosity of the formation rock, the grain density of the formation rock, and the water molar volume (block 430). The method 400 may also include determining the formation temperature at a plurality of depths (block 440). The formation temperature at the depth of interest may be measured and input in Equation (14) or calculated using Equation (15). In some embodiments, the method may further include calculating the in-situ pore pressure at a plurality of depths using Equation (14) using the mole fraction of fixed charges, the formation temperature, a surface temperature, a hydrostatic pressure, an overburden stress, and an in-situ water activity (block 450). As a result, according to the method 400, an output providing the in-situ pore pressure may be obtained that takes into account the chemical osmotic pressure (block 460). The in-situ pore pressure is then used in a wellbore stability model to monitor and maintain stability of the formation rock (block 470).

In some embodiments, an electronic device such as control terminal 250 illustrated in FIG. 1 may include a computer processor coupled to at least one logging tool (114 and/or 116), wherein the logging tool is configured to acquire well log data in a formation rock, and wherein the electronic device comprises functionality for acquiring well log data from at least one logging tool. The electronic device comprises functionality for calculating data (such as calculated data 221, 222, 223, and 224). These calculated data include a cation-exchange capacity using a volume fraction and a cation-exchange capacity for each mineral in the formation rock. These calculated data also include a mole fraction of fixed charges using the cation-exchange capacity, a porosity of the formation rock, a grain density of the formation rock, and a water molar volume. The formation temperature may also be determined either via calculation or by measurement acquired via a logging tool. The calculated data further include the in-situ pore pressure using the mole fraction of fixed charges, the formation temperature, a surface temperature, a hydrostatic pressure, an overburden stress, and an in-situ water activity. The electronic device comprises functionality for outputting the in-situ pore pressure of the formation rock. The in-situ pore pressure may be used in a wellbore stability model to monitor and maintain stability of the formation rock. When severe abnormal pressure is observed, drilling mud weight might need to be adjusted accordingly to avoid kick. In the overpressure zones, rate of penetration usually increases as the formation becomes less compacted. The drilling team should carefully accommodate the drilling operations, such as adjusting rotary speed. A severe overpressure could result in blowout of a well. Avoiding a blowout cannot be done by simply increasing mud weight because higher mud weight might fracture the formation and lost circulation occurs. In such situations, the value of pore pressure should be used in wellbore stability models to determine the safe drilling mud weight window. On the other hand, if significant under pressure is detected, drilling operations should be cautious as well to avoid stuck pipes.

In some embodiments, a non-transitory computer storage medium may include program instructions. These program instructions, when executed, may be configured to perform an embodiment method 400 illustrated in FIG. 3 for determining an in-situ pore pressure in a formation rock. The non-transitory computer storage medium allows the monitoring of a formation rock pore pressure and stability. In some embodiments, the in-situ pore pressure may be used in a wellbore stability model to monitor and maintain stability of the formation rock. When changes in the in-situ pore pressure of the rock formation are detected, characteristics of drilling fluids, well service fluids, enhanced recovery fluids, or production fluids, may be altered during drilling to maintain stability of the wellbore. In some embodiments, optimization of operations based on the in-situ pore pressure output from the non-transitory computer storage medium may include adjusting one or more operation factors. In some embodiments, the wellbore stability model from the non-transitory computer storage medium may specify one or more of a composition, a quantity, a weight, a type, and an injection pressure of drilling fluid in order to optimize drilling and/or operations.

EXAMPLE

Example 1

Figure 4:
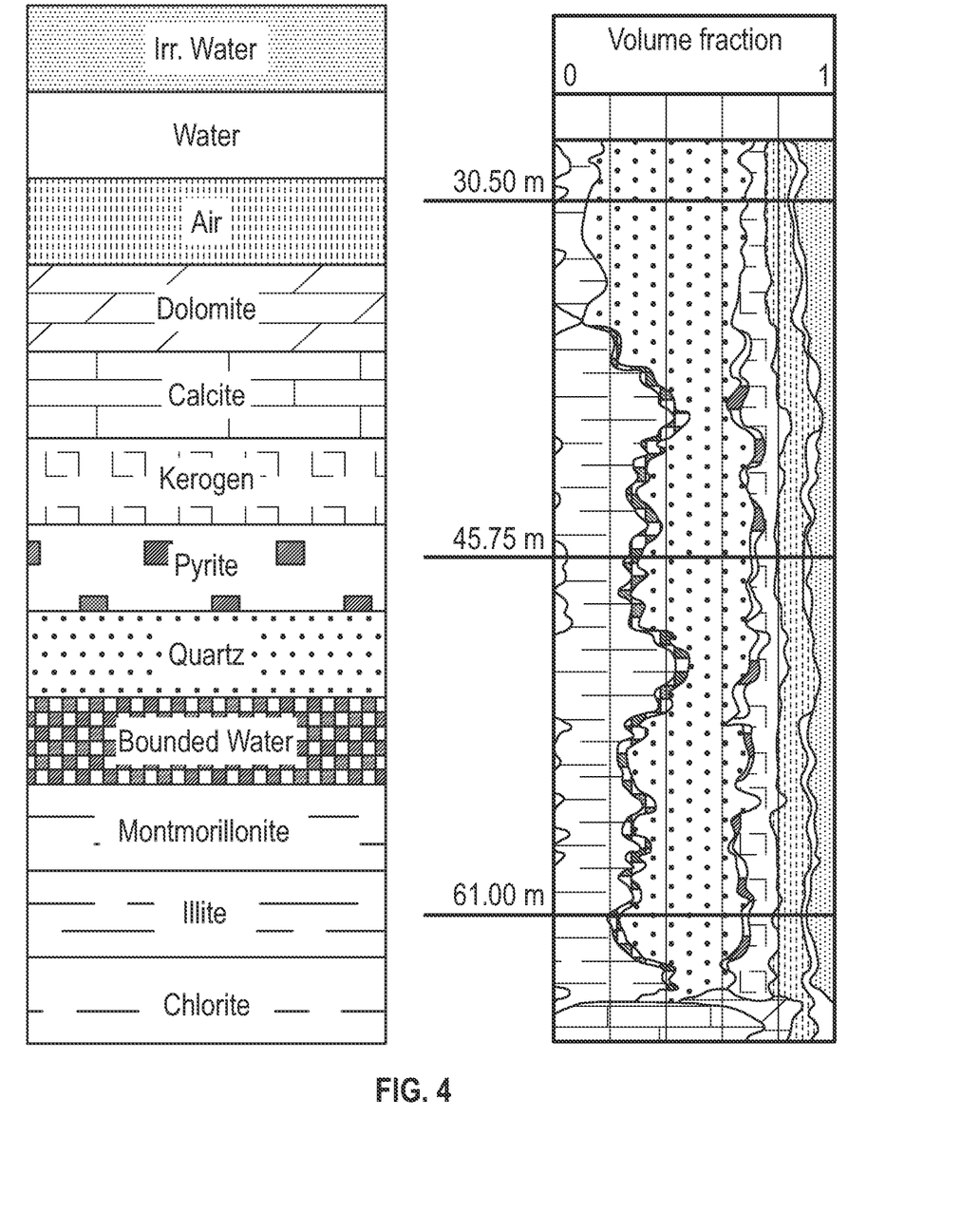
FIG. 4 shows an elemental capture spectroscopy log for a Woodford shale formation in accordance with Example 1.
Figure 5:
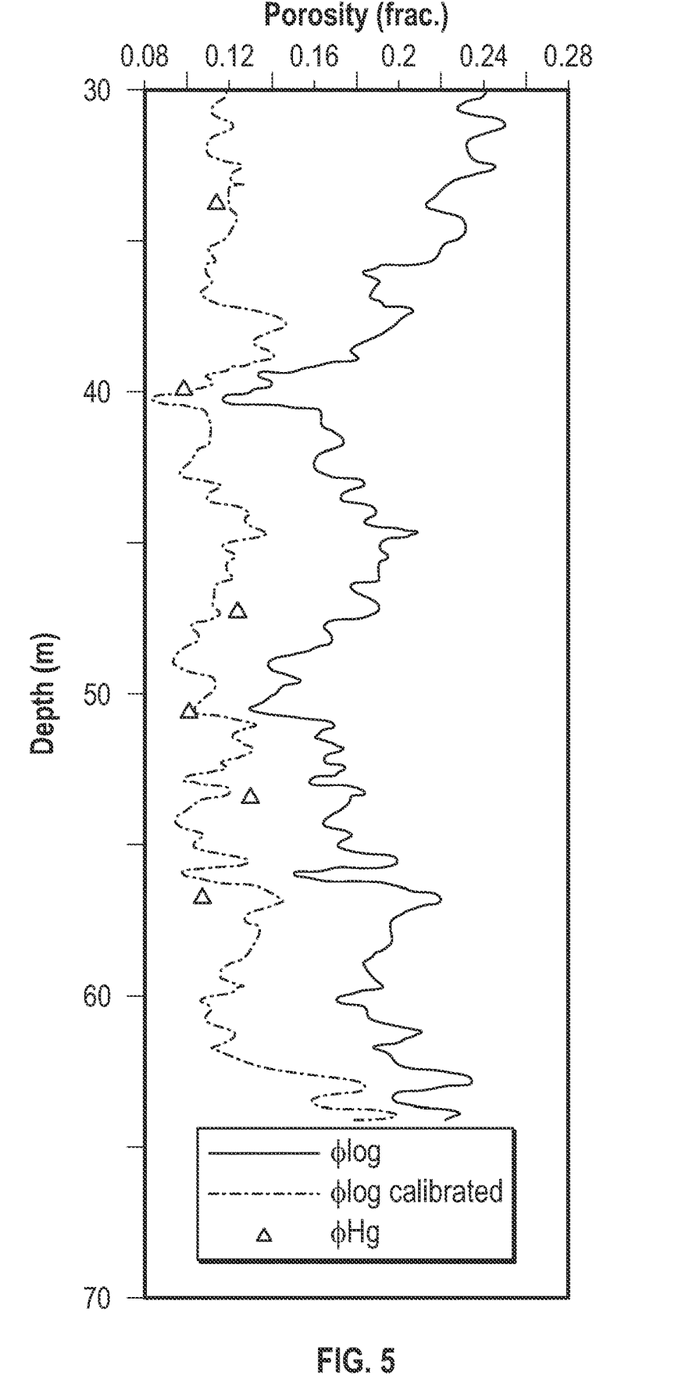
FIG. 5 shows a porosity log for the Woodford shale interval in accordance with Example 1.
Figure 6:
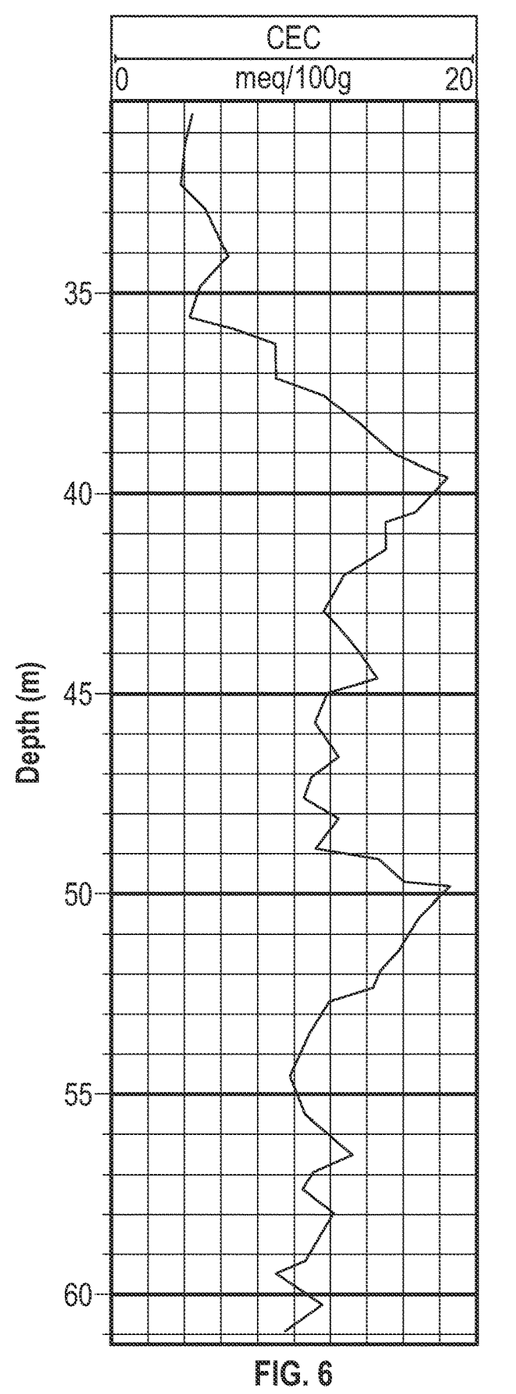
FIG. 6 is a cation exchange capacity (CEC) log for the Woodford shale interval in accordance with Example 1.
Figure 7:
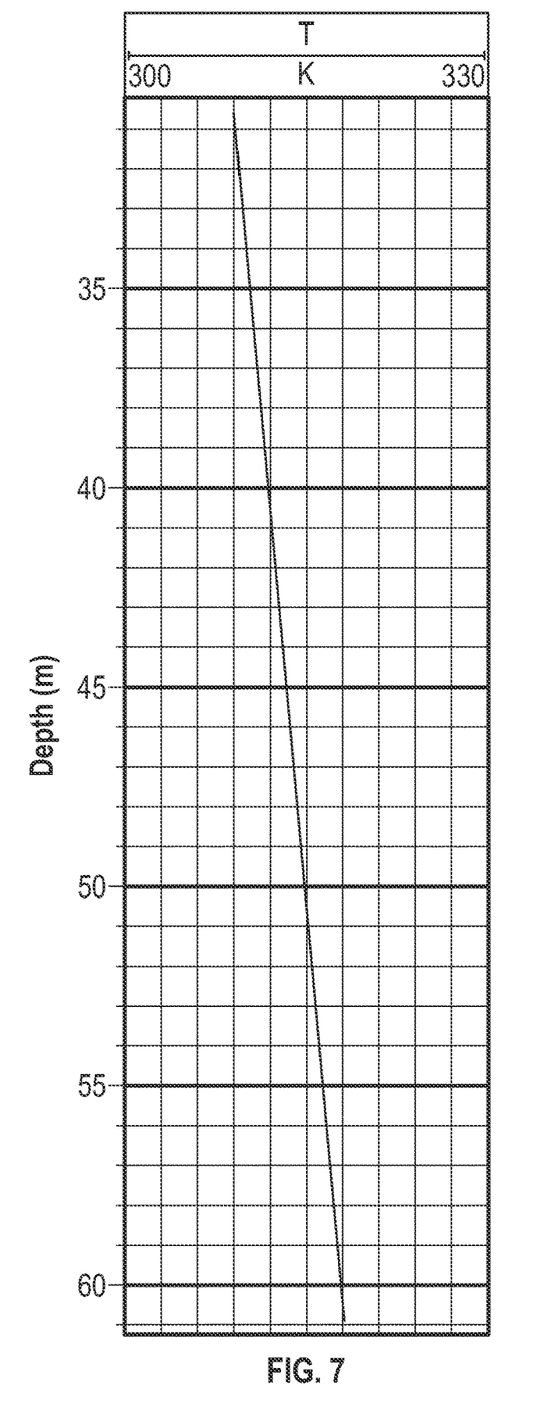
FIG. 7 shows the log of mole fraction of fixed charges in accordance with Example 1.
Figure 8:
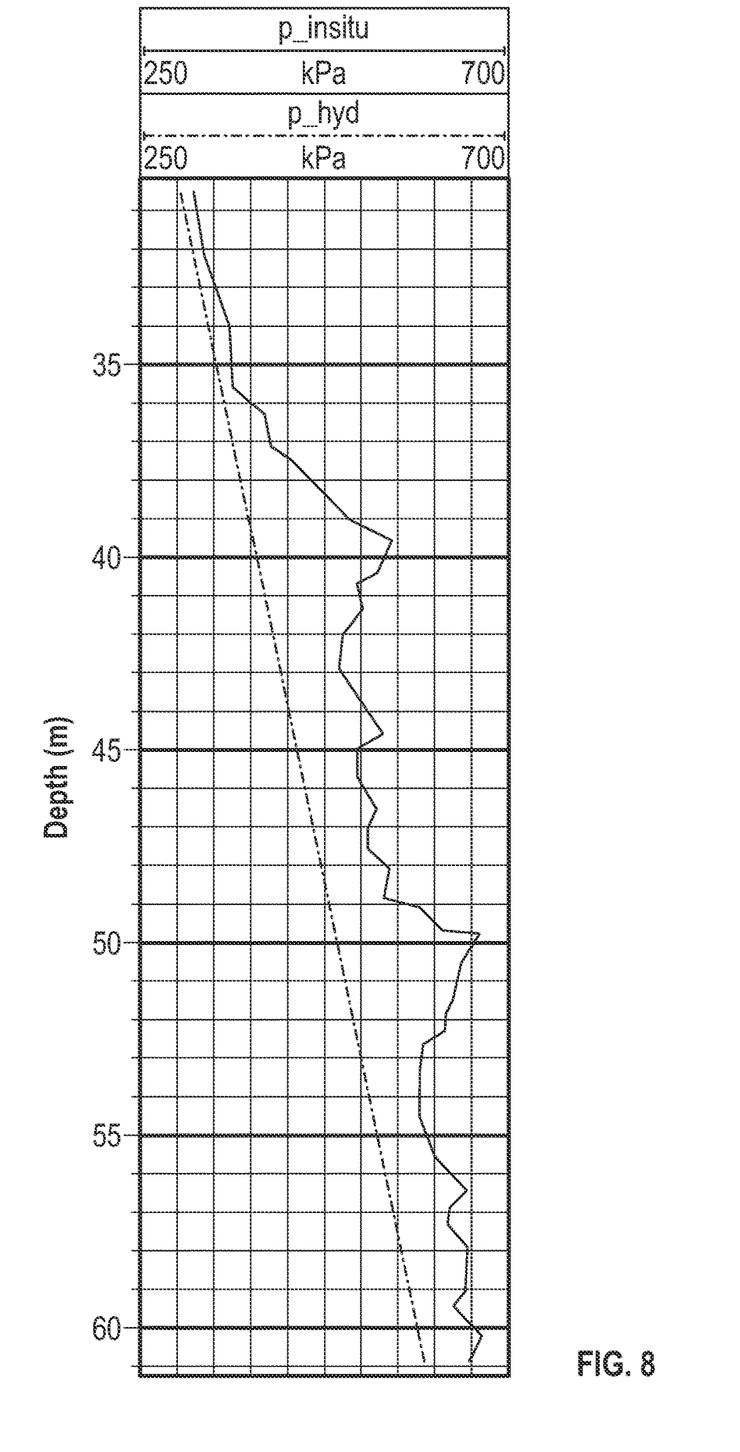
FIG. 8 shows the logs of the hydrostatic pressure and in-situ pore pressure in accordance with the method of one or more embodiments.

As an example of the method according to the present disclosure, FIG. 4 shows an ECS log obtained for a Woodford shale formation. FIG. 5 shows a porosity log of the Woodford shale formation obtained in function of the depth. Based on the CEC values provided in Table 1, FIG. 6 shows the CEC log of the Woodford shale formation in function of the depth generated from Equation (16). Using the CEC log of FIG. 6 and the porosity log of FIG. 5, the log of mole fraction of fixed charges was generated using Equation (15) and is shown in FIG. 7. In particular, at a surface temperature of 303 K, i.e., 30° C., and with a water activity of the Woodford shale of 0.6, Equations (14) was applied to calculate the in-situ pore pressure in function of the depth, and is shown in FIG. 8.

Unless defined otherwise, all technical and scientific terms used have the same meaning as commonly understood by one of ordinary skill in the art to which these systems, apparatuses, methods, processes and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

While the invention has been described with respect to a limited number of embodiments, those skilled in the art, having the benefit of this disclosure, will appreciate that other embodiments can be devised that do not depart from the scope of the invention as described herein. Accordingly, the scope of the invention should be limited only by the accompanying claims.

What is claimed is:

1. A method for determining an in-situ pore pressure and maintaining stability of a formation rock during wellbore operations, the method comprising:
   acquiring well log data from at least one logging tool, wherein well log data comprises elemental capture spectroscopy log data and/or X-ray diffraction mineralogy log data;
   calculating a cation-exchange capacity using a volume fraction and a cation-exchange capacity for each mineral in the formation rock using the well log data;
   calculating a mole fraction of fixed charges using the cation-exchange capacity, a porosity of the formation rock, a grain density of the formation rock, and a water molar volume;
   determining a formation temperature;
   calculating the in-situ pore pressure at a plurality of depths using the mole fraction of fixed charges, the formation temperature, a surface temperature, a hydrostatic pressure, an overburden stress, and an in-situ water activity;
   outputting the in-situ pore pressure of the formation rock; and
   using the in-situ pore pressure in a wellbore stability model to monitor and maintain stability of the formation rock, wherein monitoring and maintaining stability of the formation rock using the in-situ pore pressure comprises adjusting one or more of a composition of a wellbore fluid, a weight of the wellbore fluid, a type of wellbore fluid, an injection pressure of the wellbore fluid, a rotary speed of a drill bit, and a rate of penetration of a drill bit into the formation,
   wherein the calculating the in-situ pore pressure is conducted by a formula represented by:

$$p_{insitu} = p_{hyd} + (\sigma_v - p_{hyd}) \frac{T}{T_{surface}} \left[ \sqrt{(m^{fc})^2 + (1 - a_{insitu})^2} - (1 - a_{insitu}) \right]^n$$

where $p_{insitu}$ is the in-situ pore pressure, $p_{hyd}$ is the hydrostatic pressure, $\sigma_v$ is the overburden stress, T is the formation temperature, $T_{surface}$ is the surface temperature, $m^{fc}$ is the mole fraction fixed charges, $\alpha_{insitu}$ is the in-situ water activity, and n is a parameter determined by field data.

2. The method according to claim 1, wherein determining the formation temperature comprises calculating the formation temperature and/or measuring the formation temperature.

3. The method according to claim 1, wherein the well log data comprises gamma ray log data and wherein the method comprises using the gamma ray log data to determine a clay content of the formation rock.

4. The method according to claim 3, wherein calculating the cation-exchange capacity is performed using the clay content of the rock formation.

5. The method according to claim 1, wherein the method comprises determining mineral types and volume fractions for the minerals in the formation rock using the capture spectroscopy log data and/or the X-ray diffraction mineralogy log data.

6. The method according to claim 1, wherein the well log data comprises photoelectric log data, density log data, and neutron porosity log data.

7. The method according to claim 6, wherein the method comprises determining mineral types and volume fractions for the minerals in the formation rock using the photoelectric log data, the density log data, and/or the neutron porosity log data.

8. The method according to claim 1, wherein calculating the cation-exchange capacity comprises multiplying the volume fraction with the cation-exchange capacity separately for each of the minerals in the formation to obtain a cation-exchange product for each of the minerals in the formation rock and adding each product.

9. The method according to claim 1, wherein calculating the mole fraction of fixed charges comprises multiplying the cation-exchange capacity by (1−the porosity of the formation rock) by the grain density of the formation rock and by the water molar volume to obtain a mole fraction product, and dividing the mole fraction product by the porosity.

10. The method according to claim 1, wherein determining the formation temperature at a depth comprises calculating the formation temperature by multiplying the surface temperature of the formation rock by the depth and by a geothermal gradient.

11. The method according to claim 1, wherein calculating the in-situ pore pressure comprises adding a hydrostatic pore pressure and a factor calculated from the mole fraction of fixed charges, the formation temperature, the surface temperature, the hydrostatic pressure, the overburden stress, and the in-situ water activity.

\* \* \* \* \*